(12) United States Patent
Rusin

(10) Patent No.: US 6,622,728 B2
(45) Date of Patent: Sep. 23, 2003

(54) EXAMINATION RECORD AND DEVICE

(76) Inventor: James D. Rusin, 3512 Rum River Dr., Anoka, MN (US) 55303

( * ) Notice: Subject to any disclaimer, the term of this patent is extended or adjusted under 35 U.S.C. 154(b) by 0 days.

(21) Appl. No.: 10/038,979

(22) Filed: Jan. 4, 2002

(65) Prior Publication Data

US 2002/0056459 A1 May 16, 2002

Related U.S. Application Data

(63) Continuation-in-part of application No. 09/526,244, filed on Mar. 15, 2000, now Pat. No. 6,412,491.

(51) Int. Cl.$^7$ ................................................ A61B 19/00
(52) U.S. Cl. ........................................ 128/897; 128/898
(58) Field of Search ................................ 600/300, 549, 600/407, 587; 128/897, 898; 434/267; 602/41–57; 424/445; 428/36.1; 604/180

(56) References Cited

U.S. PATENT DOCUMENTS

| | | | | |
|---|---|---|---|---|
| 4,524,778 A | * | 6/1985 | Brown et al. | 600/549 |
| 4,702,736 A | * | 10/1987 | Kalt et al. | 604/180 |
| 4,737,109 A | * | 4/1988 | Abramson | 434/267 |
| 4,867,686 A | * | 9/1989 | Goldstein | 434/267 |
| 4,873,982 A | * | 10/1989 | Morrison | 600/300 |
| 5,106,629 A | * | 4/1992 | Cartmell et al. | 424/445 |
| 5,423,737 A | * | 6/1995 | Cartmell et al. | 602/57 |
| 5,874,140 A | * | 2/1999 | Wyner et al. | 428/36.1 |
| 5,894,844 A | * | 4/1999 | Rohrberg | 128/898 |
| 5,916,180 A | * | 6/1999 | Cundari et al. | 600/587 |
| 6,091,981 A | * | 7/2000 | Cundari et al. | 600/407 |
| 6,412,491 B1 | * | 7/2002 | Rusin | 128/897 |

* cited by examiner

Primary Examiner—Eric F. Winakur
Assistant Examiner—Nikita R Veniaminov
(74) Attorney, Agent, or Firm—Beck & Tysver P.L.L.C.

(57) ABSTRACT

A non-elastic, conformal translucent device bearing a grid is applied to a patient to facilitate tissue examination and reproducible lesion identification.

20 Claims, 3 Drawing Sheets

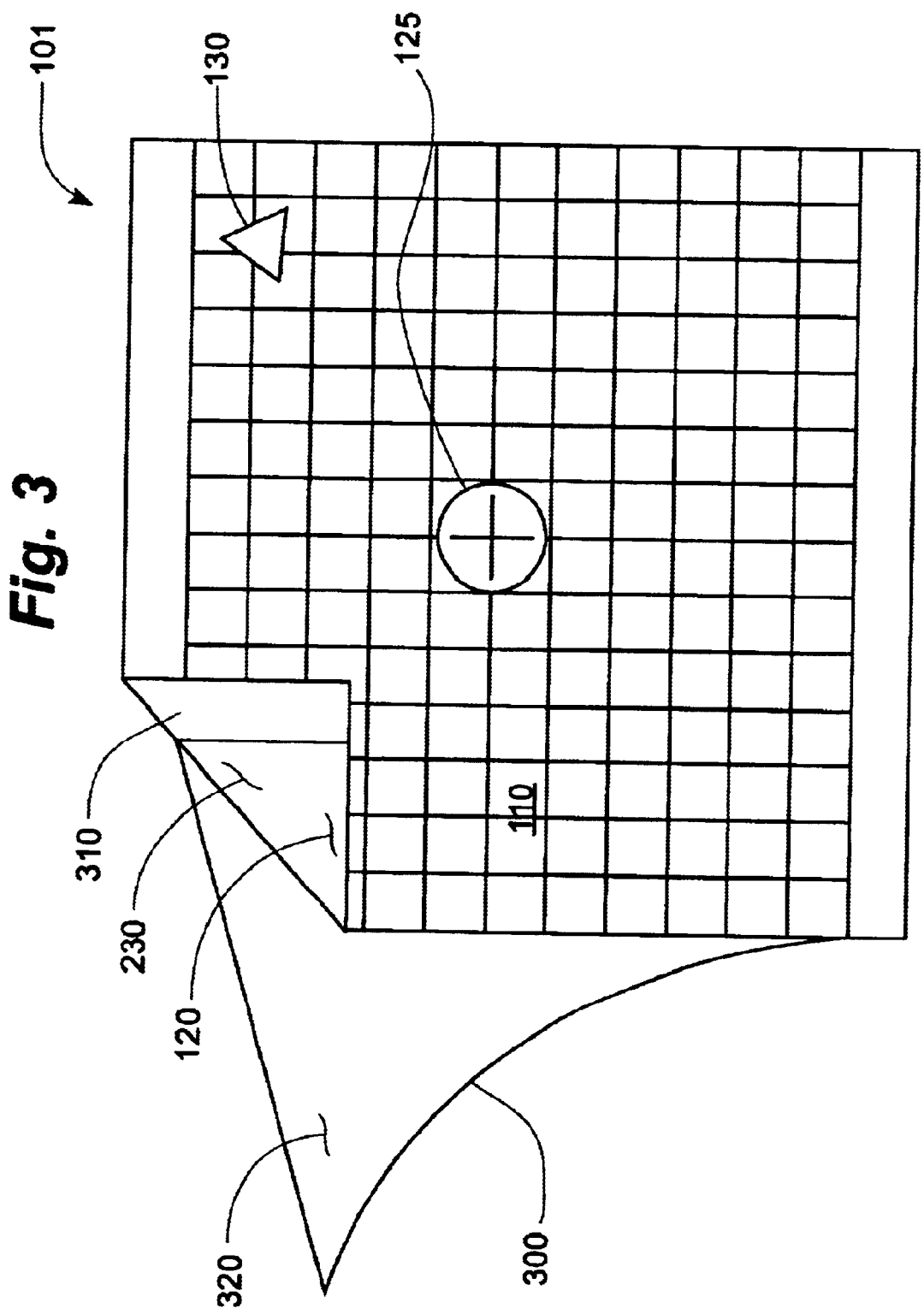

EXAMINATION RECORD AND DEVICE

This application is a continuation-in-part of U.S. Ser. No. 09/526,244, filed Mar. 15, 2000, and priority is claimed therefrom, now is a U.S. Pat. No. 6,412,491B1, issued Jul. 2, 2002.

FIELD OF THE INVENTION

The present invention relates generally to a device for facilitating breast examination and for recording the location of suspect lumps.

BACKGROUND OF THE INVENTION

Tactile physical examination of the breast is an important screen for breast cancer. The palpation or detection of lumps in the breast is the principle objective of physical examination. Both physician examination and patient self examination are widely endorsed and practiced. Early detection of lumps is desirable but difficult due to the relatively small size of emerging lumps and their location within a mass of otherwise healthy tissue. As a consequence, in many instances a single lump will be evaluated by several people to confirm detection. During this serial examination process, the suspect lump must be located repeatedly. Examiners have historically found that it is difficult to describe and record the location of the lump in an accurate manner or in a manner that will allow a subsequent examiner to find the lump reliably. Location, and subsequent re-location, is further complicated by the pliability or lack of stability of breast tissue.

There exist a number of other challenges to detecting a lump through tactile examination. For example, there is a tendency for a lump to move under the pressure of the examiner's hand during examination. Further, some modest patients are stressed by a tactile examination.

The present invention is directed to aid in recording the location of a detected lump such that the lump can be easily relocated.

SUMMARY OF THE INVENTION

The present invention is an examination device that assists in the stabilization of tissue during examination and that facilitates the reliable and convenient description of the location of a lump for subsequent relocation or treatment.

BRIEF DESCRIPTION OF THE DRAWINGS

An exemplary version of an examination device is shown in the figures wherein like reference numerals refer to equivalent structure throughout, and wherein:

FIG. 3 shows a device embodying the present invention in concert with a release liner.

DETAILED DESCRIPTION OF PREFERRED EMBODIMENT(S)

Figure 1:
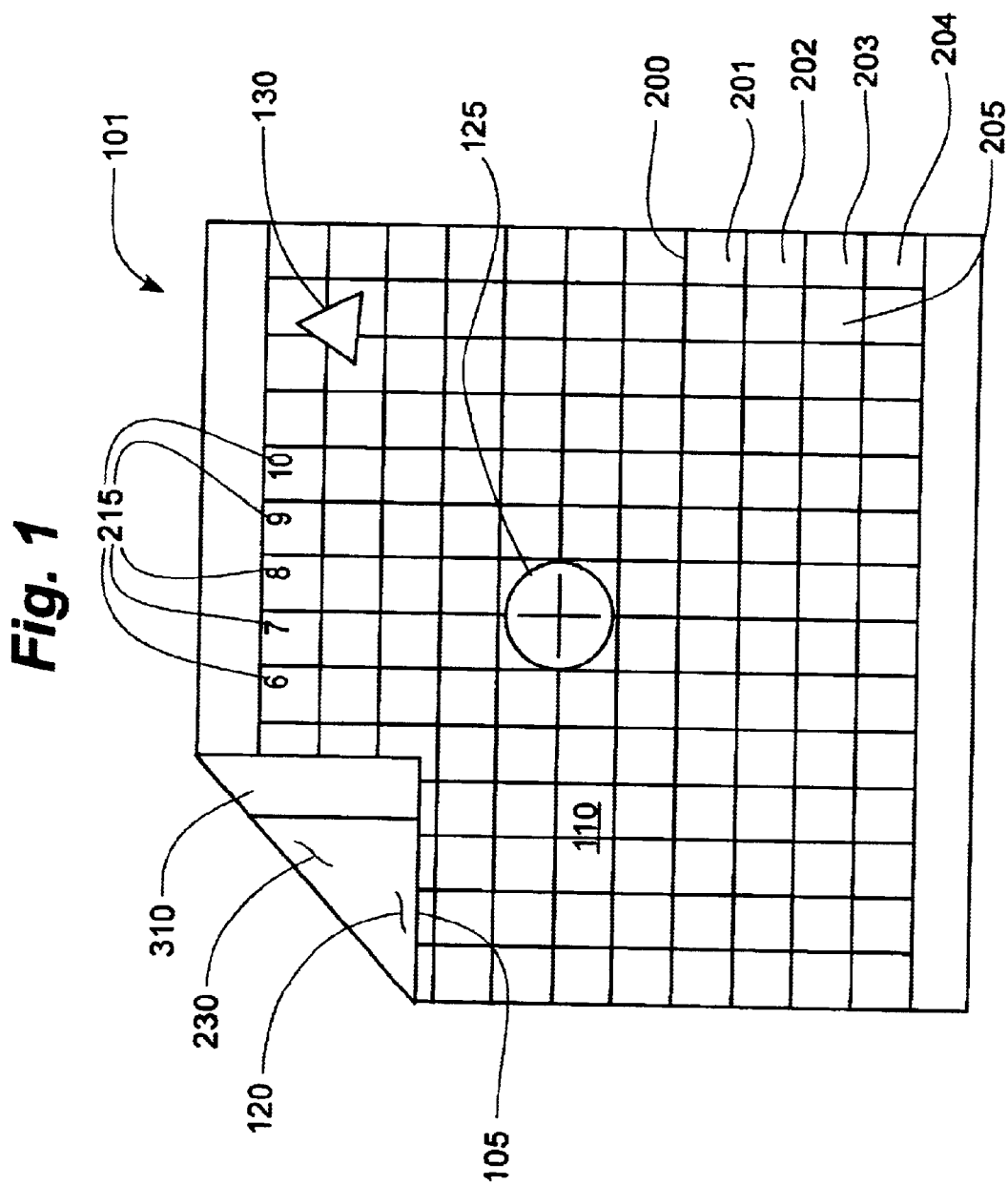
FIG. 1 shows a device embodying the present invention.
Figure 2:
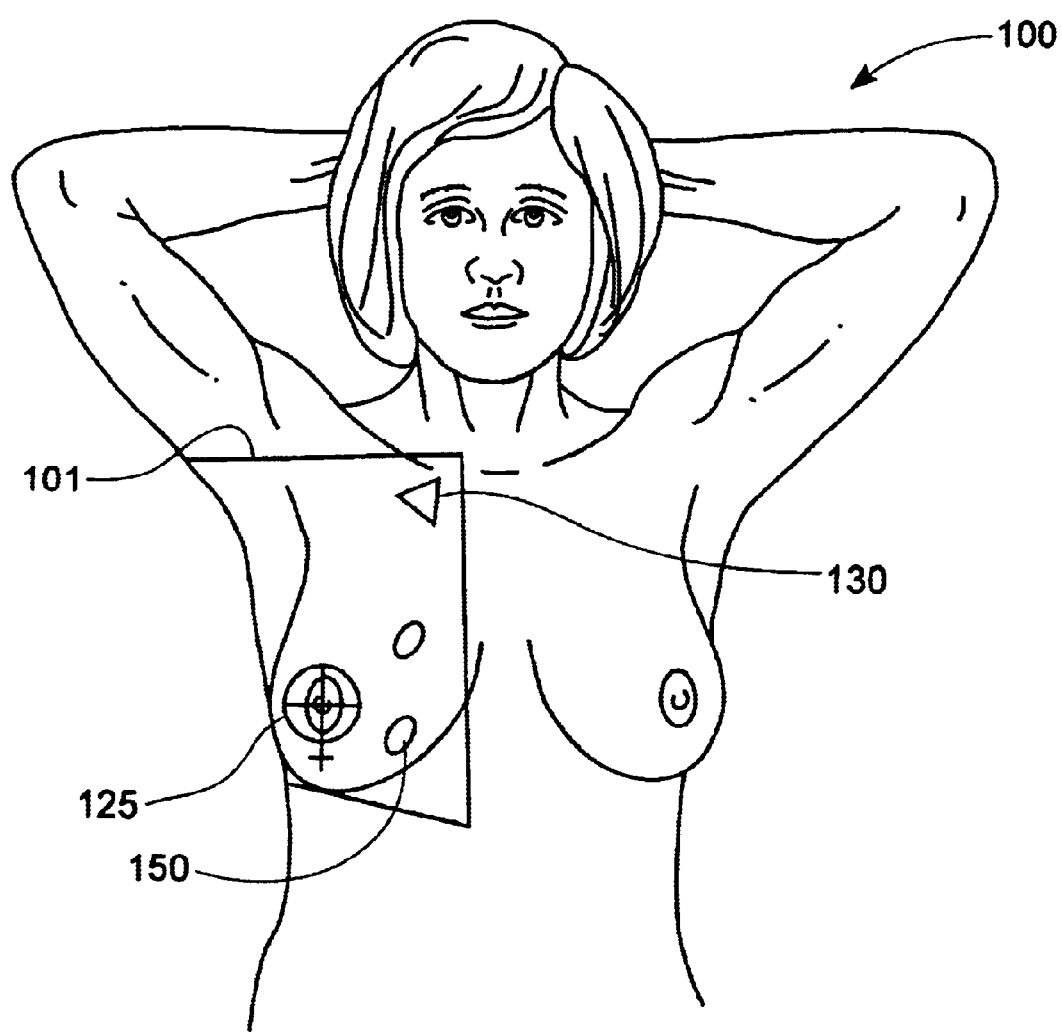
FIG. 2 shows one aspect of an illustrative method of the present invention.

FIG. 1 shows an illustrative embodiment 101 of the present invention. FIG. 2 shows the examination aid device 101 in place on a patient 100 during use. The device 101 is depicted as a transparent film for purposes of illustration. Translucent or partially opaque materials are contemplated within the scope of the invention and may be preferable. In general, polymeric films are suitable materials to create the device 101. Non-elastic materials are preferable; conformable materials are preferable.

The device 101 has one surface 120, a "lower surface", which in use is toward the patient or adjacent the patient's skin; the device 101 has an opposite "upper" surface 110. The device 101 is illustrated in FIGS. 1 and 3 with one corner 105 folded over so that both upper and lower surfaces 110, 120 are shown. Conventional surface treatments can be used to make the upper surface 110 "slippery" with a coefficient of friction sufficiently low to allow the skin of the examiner's fingers to slide over it easily for examination. Characteristics of the lower surface 120 are described below.

The device 101 has a fiducial mark 125, or a set of coordinating fiducial marks 125 and arrow 130, that establish replicable placement and orientation of the device on the patient. For example, in use, the fiducial mark can be placed in registration with an identifiable location on the patient's body such as on the nipple, while arrow 130 points toward the patient's head.

As illustrated in FIG. 1, the device 101 bears a grid 200 defining grid cells. Reference numerals 201–205 identify examples of five such grid cells. While the cells may be of any size, within the spirit of this invention, cells in a preferred embodiment have a size of between about one half inch by one half inch, and two inches by two inches. It is not required that the cells be square. In the embodiment illustrated in FIGS. 1 and 3, the grid 200 is apparent on the upper surface 110; however, it will be understood that the grid 200 might be apparent on the lower surface 120, particularly when the device 101 is made of a translucent or transparent material.

The grid cells may contain alphanumeric symbols for labeling the cell, i.e. "cell labels" 215, and preferably each alphanumeric marker is unique to its associated cell. For example, the cells might be serially numbered. Further, the serial numbers may be sequential. In the illustration of FIG. 1, five example cells bear cell labels 215. Typically, all cells would bear cell labels. In an alternate embodiment, a coordinate system may be used by which rows are uniquely labeled and columns are uniquely labeled, and the cell label for each cell is a combination of its row and column identifiers.

The lower surface 120 of the device 101 includes a major region 230 that is non-adhesive. At least a portion of region 230 may have a "tacky" feel with a coefficient of friction sufficient to allow the surface to resist movement across the skin. The lower surface 120 further includes a relatively small adhesive region 250 which, in use, allows the aid 101 to be removably adhered to the patient's skin during examination. In one embodiment, a strip region along each edge of the device 101 is adhesive. In another embodiment, strip regions along two edges of the device 101 are adhesive. In yet another embodiment, a region in registration with the fiducial marker 125 is adhesive. In other embodiments, any combination of adhesive regions may be employed.

The device embodying the present invention may also include a marker 150 attachable to the device 101 for identification of a location of interest, such as a lump, on the portion of the human body under examination. Marker 150 is illustrated in FIG. 2. The attachable marker 150 may be an adhesive label. The marker may be permanent so that the marker 150 cannot be repositioned, particularly unintentionally, without destroying the device 101. Marking pens may also be used to generate a marker 150 on the device 101. In addition, the cell label can be recorded, such as in the patient's examination records, and used for subsequent location of the point of interest.

As illustrated in FIG. 2, the method of the present invention includes using the device 101 in the tactile examination of a portion of the human body such as a breast. In an illustrative method of the present invention, the examiner (e.g. a physician conducting a tactile breast examination on a patient or a patient conducting a self exam) places a device 101 over the portion of the human body of interest. The device is positioned such that the fiducial mark 125 aligns with an identifiable and generally immutable feature of the human body, such as a nipple. When using an embodiment of a device 101 that includes one or more adhesive regions on surface 120, the adhesive region is pressed to adhere to the human body.

The examiner slides the examining hand across the top surface 110 of the device 101 while applying pressure. The slippery texture of the surface 110 allows the hand to slide easily over the examination area, without dislodging or moving the device 101 out of position.

When a feature of interest, such as a lump, is sensed by the examiner, the examiner marks the point of interest on the device 101 with marker 150. In addition, the examiner may record the cell label 215 in the patient's medical or examination record. Upon completion of the examination, the device 101 can be folded and stored in the patient's paper medical record for later reference. The marker 150 or the cell label 215 or both 150, 215 can then be used by others to subsequently locate the feature of interest in an efficient and reliable manner. In the absence of the original device 101, the cell label 215 can be used to identify the location of the lump using a second device bearing the same grid and fiducial markings 125 as the original device 101.

For subsequently locating the feature of interest, the device 101 can be fitted again on the patient 100, using the fiducial mark 125 and orientation mark 130 to place the device 101 in the same position as during the original fitting. As noted above, the device 101 is preferably of an inelastic material, but is sufficiently conformal to allow the reapplication process to reposition the fiducial mark 125 and orientation mark 130 to reposition the markers in the same location as the original fitting.

In this manner, the device 101 serves as a tool to communicate the location of the feature of interest to subsequent examiners. For example, if a lump is found by the patient during self examination, the device 101 is used to "show" the patient's doctor the location of the lump via the marker 150 or the cell label 215 or both 150, 215. As another example, if a lump is found by the patient's doctor during examination, the device 101 allows the oncologist or a radiologist to efficiently find the lump.

Multiple devices 101 can be conveniently packaged together, such as stacked in layers or dispensed from a roll, with one device 101 perforatedly attached to an adjacent device 101. As illustrated in FIG. 3, a release liner 300 is removably coupled to a device 101, and this release liner 300 prevents the adhesive region 250 of one device 101 from sticking to an adjacent device 101. The release liner 300 may have distinct separable regions 310, 320, with one such region 310 registering with the adhesive region 250 of the accompanying device 101. In the illustration of FIG. 3, region 310 is depicted in attachment with device 101, while region 320 is depicted peeled away from device 101.

In use, when one device 101 with its associated liner 300 is prepared for use, the region 320 of the liner 300 that is registered with the non-adhesive portion 230 of the device 101 is removed or peeled away, leaving another region 310 of the liner 300 still adhered to the adhesive region 250 of the device 101. With the adhesive region 250 of the device 101 covered by a liner region 310, the device 101 can be easily moved about the patient's body until it is properly positioned. When properly positioned, the liner region 310 can then be removed so that the adhesive region 250 of the device 101 can be adhered to the patient 100 stabilizing the underlying tissue.

Although an illustrative version of the device is shown, it should be clear that many modifications to the device may be made without departing from the scope of the invention.

What is claimed is:

1. An examination device for use during tactile examination of a patient, comprising a film bearing the image of a grid and having a first surface having a first coefficient of friction that is generally slippery to allow an examiner's hand to slide easily over said first surface during tactile examination and a second opposite surface having a second coefficient of friction that is higher than the first coefficient of friction, said second coefficient of friction being sufficient to inhibit relative motion between said film device and the patient's skin, said lower surface including an adhesive region sufficiently adhesive to removably affix the film to the patient.

2. An examination aid according to claim 1, wherein said device is of sufficient size to cover a human breast.

3. An examination aid according to claim 2, wherein said film is between about 12–16 inches by between about 12–16 inches.

4. An examination aid according to claim 1, wherein said grid defines grid cells and includes alphanumeric markings associated with said grid cells.

5. An examination aid according to claim 4, wherein said alphanumeric markings are unique to each respective grid cell.

6. An examination aid according to claim 1, wherein said grid defines grid cells that are about 1 inch by about 1 inch.

7. An examination aid according to claim 1, wherein said film bears a fiducial marker.

8. An examination aid according to claim 1, wherein a region of said film is non-opaque.

9. An examination aid according to claim 8, wherein a region of said film is translucent.

10. An examination aid according to claim 8, wherein a region of said film is transparent.

11. An examination aid according to claim 1, wherein said film has a thickness of between about 0.5 and 2 mils.

12. An examination aid according to claim 1, wherein said film is conformable.

13. An examination aid comprising a film bearing a grid and having a first surface having a first coefficient of friction that is generally slippery to allow an examiner's hand to slide easily over said first surface during tactile examination and a second opposite surface having a second coefficient of friction that is higher than the first coefficient of friction, said second coefficient of friction being sufficient to inhibit relative motion between said film device and the patient's skin, said lower surface including an adhesive region sufficiently adhesive to removably affix the film to the patient, and a liner sheet removably adhered to said adhesive region.

14. An examination aid according to claim 13 wherein said liner sheet includes a first portion that adheres minimally to the non-adhesive region of the film and a second portion separable from said first portion that adheres to said adhesive region.

15. An examination aid according to claim 14, wherein said liner sheet is in registration with said film such that said first portion is in registration with said non-adhesive region of the film and said second portion is in registration with said adhesive portion of said film.

16. A method for tactile examination of a patient, comprising the steps of:
  a) providing a film device having upper and lower surfaces, said upper surface having a first coefficient of friction, said lower surface having a second coefficient of friction that is higher than the first coefficient of friction, said second coefficient of friction being sufficient to inhibit relative motion between said film device and the patient's skin, said lower surface including an adhesive region sufficiently adhesive to removably afix the film device to the patient;
  b) placing the film device over the portion of the patient's body so that the lower surface of the film device is in contact with the skin of the patient;
  c) temporarily pressing the adhesive region against the skin to enable it to adhere thereto;
  d) sliding the examining hand across said upper surface of the film device while applying pressure to said upper surface of the film device with the examining hand.

17. A method according to claim 16, further comprising the step of:
  e) upon identifying a feature of interest during step d, placing a mark on said film device in registration with the feature of interest.

18. A method according to claim 16, wherein said film device bears a grid defining grid cells each bearing a unique label, and said method comprising the steps of:
  f) upon identifying a feature of interest during step d, recording the location using said label of the grid cell in registration with the feature of interest.

19. An examination device for use during tactile examination of a patient, comprising a film having a first surface having a first coefficient of friction that is generally slippery to allow an examiner's hand to slide easily over said first surface during tactile examination and a second opposite surface having a second coefficient of friction that is higher than the first coefficient of friction, said second coefficient of friction being sufficient to inhibit relative motion between said film device and the patient's skin.

20. An medical examination device according to claim 19, said film bearing uniquely labeled grid cells.

* * * * *